United States Patent
Wei et al.

(10) Patent No.: US 10,106,499 B1
(45) Date of Patent: Oct. 23, 2018

(54) PROCESSES FOR PREPARING CYCLOPENTA[B]NAPHTHALENOL DERIVATIVES AND INTERMEDIATES THEREOF

(71) Applicant: CHIROGATE INTERNATIONAL INC., Yangmei (TW)

(72) Inventors: Shih-Yi Wei, Yangmei (TW); Shih-Hsun Su, Yangmei (TW)

(73) Assignee: CHIROGATE INTERNATIONAL INC., Tangmei (TW)

( * ) Notice: Subject to any disclaimer, the term of this patent is extended or adjusted under 35 U.S.C. 154(b) by 0 days.

(21) Appl. No.: 15/809,002

(22) Filed: Nov. 10, 2017

(51) Int. Cl.
C07C 315/04 (2006.01)
C07C 67/297 (2006.01)
C07C 405/00 (2006.01)
C07C 39/23 (2006.01)
A61K 31/5575 (2006.01)

(52) U.S. Cl.
CPC ........ *C07C 405/0083* (2013.01); *C07C 39/23* (2013.01); *C07C 67/297* (2013.01); *C07C 315/04* (2013.01); *A61K 31/5575* (2013.01)

(58) Field of Classification Search
CPC ... C07C 315/04; C07C 405/008; C07C 39/23; C07C 67/297; C07C 45/59
See application file for complete search history.

(56) References Cited

U.S. PATENT DOCUMENTS 8,524,939 B2 * 9/2013 Wei .................. C07C 67/297
560/102

* cited by examiner

*Primary Examiner* — Yate' K Cutliff
(74) *Attorney, Agent, or Firm* — Ladas & Parry LLP

(57) ABSTRACT

Novel processes for preparing cyclopenta[b]naphthalenol derivatives of Formula 1

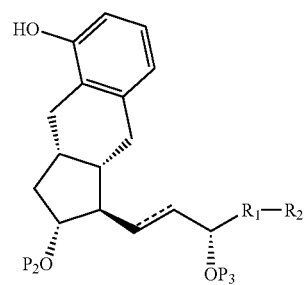

which are useful for the synthesis of corresponding benzindene prostaglandins are provided. The present invention also relates to novel intermediates prepared from the processes.

10 Claims, No Drawings

PROCESSES FOR PREPARING CYCLOPENTA[B]NAPHTHALENOL DERIVATIVES AND INTERMEDIATES THEREOF

FIELD OF THE INVENTION

The present invention relates to improved, commercially available and industrially advantageous processes for preparing cyclopenta[b]naphthalenol derivatives of Formula 1

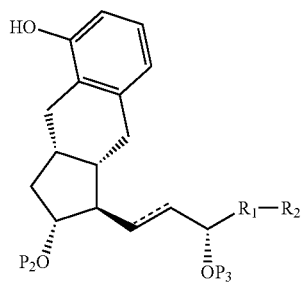

1 which are useful for the synthesis of corresponding benzindene prostaglandins. The present invention also relates to novel intermediates prepared from the processes.

BACKGROUND OF THE INVENTION

Benzindene prostaglandins are known to be useful to treat a variety of conditions. Cyclopenta[b]naphthalenol derivatives of Formula 1

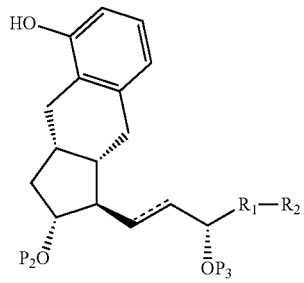

1 are key intermediates for the synthesis of benzindene prostaglandins. As shown in Scheme A, Aristoff et al. discloses in Tetrahedron Letters (1982), 23(20), 2067-2070 that a compound of Formula 1a can be obtained by sulfonylation of a compound of Formula 4a to form a compound of Formula 3a (Step a), removing the protecting group on the phenol group, i.e., tert-butyldimethylsilyl, for forming a compound of Formula 2a (Step b), and intramolecular alkylation of the compound of Formula 2a (Step c):

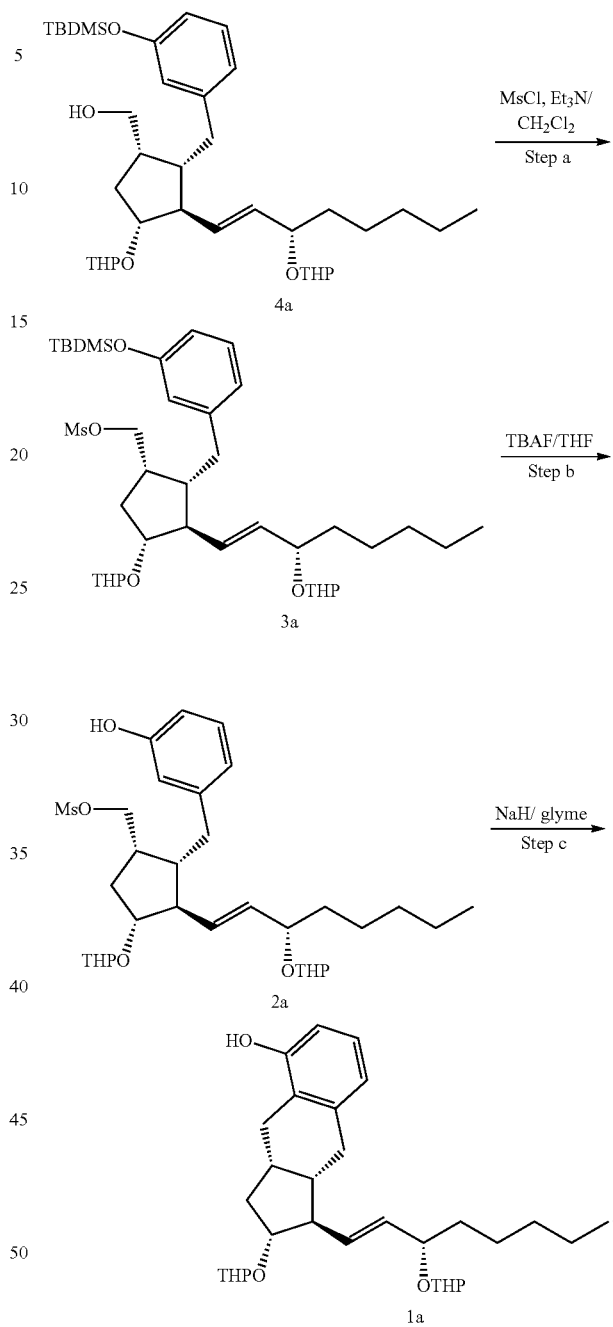

A similar process for the preparation of the cyclopenta[b]naphthalenol derivatives is also reported in U.S. Pat. No. 8,524,939. As shown in Scheme B, the compound of Formula 1b can be obtained by sulfonylation of a compound of Formula 4b (Step a) to form a compound of Formula 3b (Step a), removing the protecting group on the phenol group, i.e., benzyl, for forming a compound of Formula 2b (Step b), and intramolecular alkylation of the compound of Formula 2b:

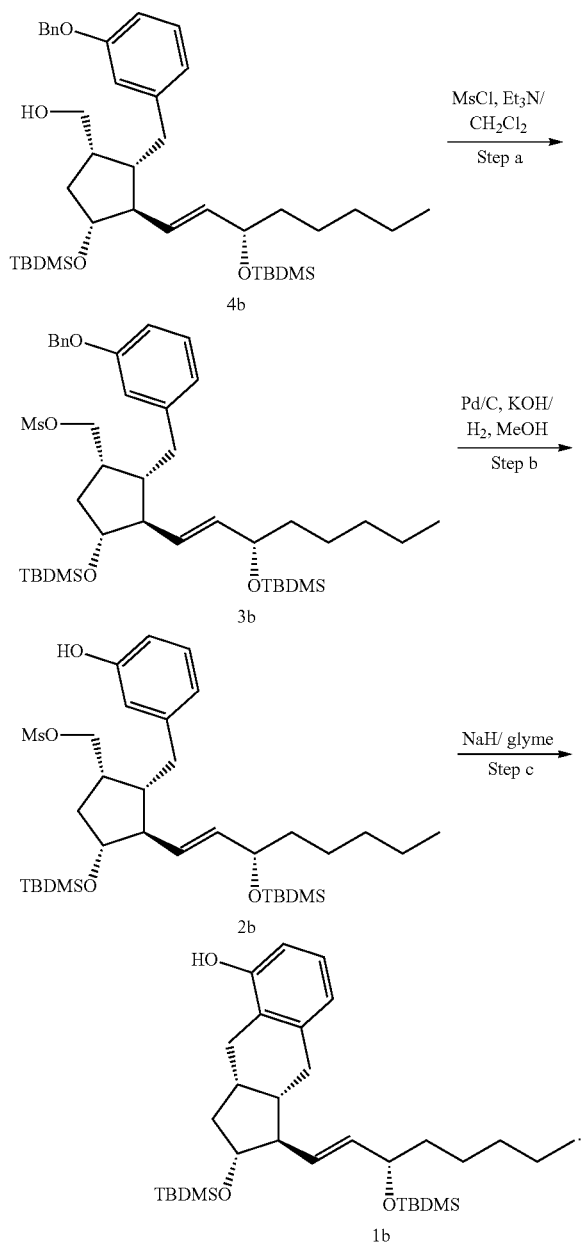

Scheme B

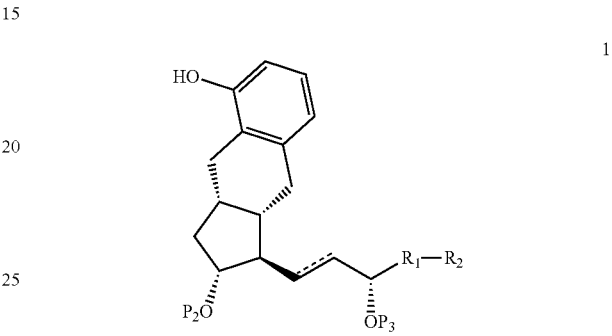

has to be used in step b of Scheme B to allow the hydrogenation reaction for removing the benzyl group to be successfully carried out.

Consequently, there is a demand for processes for the preparation of the compound of Formula 1 that are commercially available of high yield and at a low cost and are more convenient to operate.

SUMMARY OF THE INVENTION

The present invention provides novel and improved processes of preparing the cyclopenta[b]naphthanol derivatives of Formula 1 wherein $R_1$ is a single bond, $C_{1-4}$-alkylene or —$CH_2O$—; $R_2$ is $C_{1-7}$-alkyl, aryl or aralkyl, each of which is unsubstituted or substituted by $C_{1-4}$-alkyl, halogen or trihalomethyl; $P_2$ and $P_3$ are the same or different protecting groups for the hydroxyl groups; and === is a single bond or a double bond, which solve the drawbacks associated with the prior processes.

The present invention also provides novel intermediates for the synthesis of the benzindene prostaglandins.

DETAILED DESCRIPTION OF THE INVENTION

Herein, unless otherwise specified, the term "alkyl" refers to an aliphatic hydrocarbon group which may be straight or branched having 1 to 12 carbon atoms, preferably 1 to 8 carbon atoms, and more preferably 1 to 6 carbon atoms, in the chain, such as methyl, ethyl, n-propyl, iso-propyl, t-butyl, and the like; the term "aryl" refers to a monocyclic or polycyclic aromatic hydrocarbon radical, such as phenyl, naphthyl, anthryl, phenanthryl and the like, which may optionally be substituted with one or more substituents, including but not limited to, halogen, alkoxyl, thioalkoxyl, alkyl, and aryl; and the term "aralkyl" refers to a straight or branched hydrocarbon containing 1 to 20 carbon atoms and one or more aryl group as described above, such as benzyl, benzhydryl, fluorenylmethyl, and the like.

When a defined radical is substituted, the substituent is selected from the group consisting of halogen, alkyl, aryl, alkoxyl, aryloxy, thioalkoxyl, thioaryloxy, alkylamino, arylamino, cyano, nitro, alkoxycarbonyl, arylcarbonyl, arylaminocarbonyl, alkylaminocarbonyl, and carbonyl or a heterocyclic group selected from the group consisting of pyridinyl, thiophenyl, pyranyl, furanyl, imidazolyl, morpholinyl, oxazolinyl, piperidinyl, piperazinyl, tetrahydropyranyl, pyrrolidinyl, pyrrolidinonyl, and the like, and the combinations thereof.

In the depiction of the compounds given throughout this description, a thickened taper line (▬◀) indicates a sub- In the aforementioned prior art procedures, in order to allow the sulfonyl group attaching to the primary alcohol, the sulfonylation reaction has to be carried out first and the protecting group on the phenyl group is removed subsequently. However, since the sulfonation products, i.e., the compounds of Formulae 3a and 3b, are unstable and have high activity, the processes suffer from disadvantages that while removing the protecting group on the phenol group, side reactions happen that cause the sulfonyl group to be detached from the primary alcohol or be replaced. Thus, the processes can only achieve a low yield, thus increasing the cost for removing side products.

In addition, the sulfonyl group of the compound of Formula 3b would undesirably affect the activity of the hydrogenation catalysts. Therefore, a large amount (such as about 30 to 40% w/w) of expensive hydrogenation catalysts stituent in the beta-orientation (above the plane of the molecule or page), and a broken flare line ("''''II') indicates a substituent in the alpha-orientation (below the plane of the molecule or page).

According to one aspect and as shown in the following Scheme C, there is provided a process for preparing the compound of Formula 1

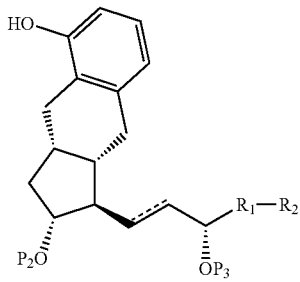

wherein $R_1$ is a single bond, $C_{1-4}$-alkylene or —$CH_2O$—; $R_2$ is $C_{1-7}$-alkyl, aryl or aralkyl, each of which is unsubstituted or substituted by $C_{1-4}$-alkyl, halogen or trihalomethyl; $P_2$ and $P_3$ are same or different protecting groups for the hydroxyl group; and === is a single bond or a double bond, prepared from cyclopentanes of Formula 4 wherein $P_1$ is a protecting group for the phenol group.

Suitable protecting groups for the phenol group are preferably acid stable and include, but are not limited to, unsubstituted or substituted alkyl, allyl, unsubstituted or substituted aryl, unsubstituted or substituted heterocyclic group, acetyl, and alkylcarbonyl, for example, benzyl, methoxymethyl, methoxythiomethyl, 2-methoxyethoxymethyl, bis(2-chloroethoxy)methyl, tetrahydropyranyl, tetrahydrothiopyranyl, 4-methoxytetrahydropyranyl, 4-methoxytetrahydrothiopyranyl, tetrahydrofuranyl, tetrahydrothiofuranyl, 1-ethoxyethyl, 1-methyl-1-methoxyethyl, triphenylmethyl, and $SiR_aR_bR_c$ wherein $R_a$, $R_b$ and $R_c$ are each independently unsubstituted or substituted alkyl, unsubstituted or substituted aryl or acetyl, such as phenyl, benzyl, substituted phenyl and substituted benzyl; and more preferably $P_1$ is selected from unsubstituted or substituted benzyl and $SiR_aR_bR_c$ wherein $R_a$, $R_b$ and $R_c$ are each independently alkyl or alkylcarbonyl.

Suitable protecting groups for the hydroxyl group are the same or different and are preferably base stable, and include, but are not limited to, methoxymethyl, methoxythiomethyl, 2-methoxyethoxymethyl, bis(2-chloroethoxy)methyl, tetrahydropyranyl, tetrahydrothiopyranyl, 4-methoxytetrahydropyranyl, 4-methoxytetrahydrothiopyranyl, tetrahydrofuranyl, tetrahydrothiofuranyl, 1-ethoxyethyl, 1-methyl-1-methoxyethyl, triphenylmethyl, and $SiR_aR_bR_c$ wherein $R_a$, $R_b$ and $R_c$ are each independently unsubstituted or substituted alkyl or unsubstituted or substituted aryl, such as phenyl, benzyl, substituted phenyl and substituted benzyl.

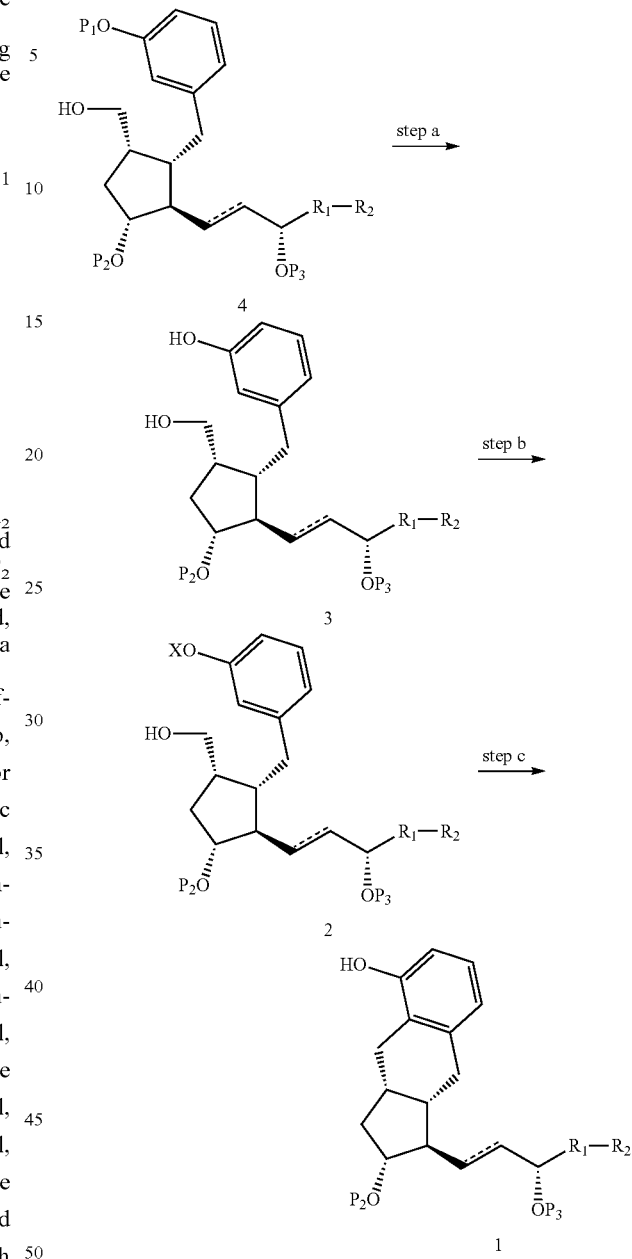

Scheme C

As shown in Step (a) of Scheme C, the compound of Formula 4 is subjected to a deprotection reaction or subjected to the deprotection reaction together with a hydrogenation of the double bond of the co-side chain for replacing $P_1$ with H. The conditions suitable for the deprotection depend on the variable of $P_1$. When $P_1$ is trialkylsilyl, the deprotection reaction is achieved by using a fluoride ion, such as tetra-butylammonium fluoride. When $P_1$ is unsubstituted or substituted benzyl, the deprotection reaction is achieved by using a hydrogenation catalyst in a suitable solvent and in the presence of hydrogen. Suitable hydrogenation catalyst contains a metal selected from the group consisting of palladium, platinum, rhodium, and nickel and a mixture thereof. Examples of the catalyst include Pd/C, Pt/C, and Ni. Suitable solvent can be selected from tetrahydrofuran, ethyl acetate, methanol, ethanol, toluene, and a mixture thereof. In one embodiment, for the compound of Formula 4 where P₁ is unsubstituted or substituted benzyl and ══ is a double bound, the hydrogenation may be ended with obtaining a diol compound of Formula 3 where ══ is a double bound, or may be continuously proceeded to obtain a diol compound of Formula 3 where ══ is a single bound, as monitored by HPLC or TLC.

As shown in Step (b) of Scheme C, the diol compound of Formula 3 is further subjected to a sulfonylation reaction to obtain a cyclopentane compound of Formula 2 wherein X is a sulfonyl group which is unsubstituted or substituted, including, but not limited to alkylsulfonyl, arylsulfonyl or aralkylsulfonyl, such as methanesulfonyl or p-toluenesulfonyl. The sulfonylation reaction is achieved in the presence of a base, such as an amine, e.g., triethylamine or N,N-diisopropylethylamine; or an nitrogen-containing heterocyclic compound, e.g., pyridine or imidazole; or an alkali metal hydride, e.g., sodium hydride, potassium hydride or lithium hydride, by using an appropriate sulfonyl donor, such as methanesulfonyl chloride or p-toluenesulfonyl chloride. In Step (b), based on the structure of the compound of Formula 3, the hydroxy group on the phenyl group has higher activity than that on the primary alcohol and thus will be primarily subjected to the sulfonylation reaction so as to form the compound of Formula 2. If an excess amount of the sulfonyl donors is used, a disulfonyl compound of Formula 2c

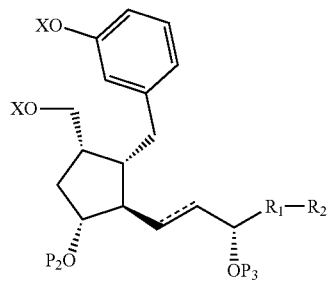

2c wherein X is alkylsulfonyl, arylsulfonyl or aralkylsulfonyl is obtained

The side products, the disulfonyl compound of Formula 2c, can be removed by a conventional method, such as column chromatography. However, since both of the main products of Formula 2 and the side products of Formula 2c can undergo the subsequent intramolecular alkylation for forming the compound of Formula 1, it is unnecessary to remove the side products, e.g., the disulfonyl compound of Formula 2c at this stage.

As shown in Step (c) of Scheme C, the compound of Formula 2 or the mixture of the compound of Formula 2 and the compound of Formula 2c is further subjected to an intramolecular alkylation so as to form the compound of Formula 1. The intramolecular alkylation is achieved by using a suitable base in a suitable solvent. Suitable base can be selected from sodium hydride, potassium hydride, lithium hydride, potassium tert-butoxide, butyllithium, and a mixture thereof. Suitable solvent can be selected from tetrahydrofuran, 2-methyl tetrahydrofuran, glyme, toluene, and a mixture thereof.

In the aforementioned prior art procedures as shown in Scheme A and Scheme B, the intramolecular alkylation is carried out on the sulfonyl group on the primary alcohol of the compounds of Formulae 2a and 2b. However, the present inventors have unexpectedly found that the intramolecular alkylation can also be carried out on the sulfonyl group on the phenol group of the compound of Formula 2.

It has also been surprisingly found that the novel process produces the product with a higher yield and reduced cost. Specifically, a large amount (about 30 to 40% w/w) of expensive hydrogenation catalysts has to be used in Step b of Scheme B of the aforementioned prior art process; however, in the novel process, only about 5 to 10% w/w of the hydrogenation catalyst is used in Step (a) of Scheme C, the benzyl groups can be rapidly removed. Moreover, the aforementioned side reactions in Step b of Scheme B can be completely avoided in the novel processes, thereby the drawbacks associated with the prior processes can be effectively solved.

The present invention further pertains to a novel compound of Formula 3a

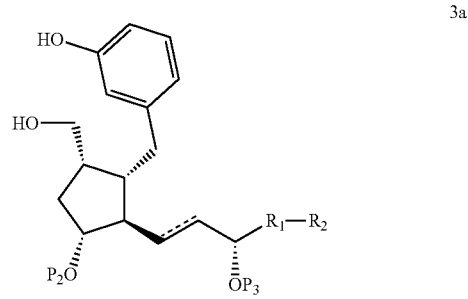

3a wherein R₁ is a single bond, $C_{1-4}$-alkylene or —CH₂O—, preferably methylene; R₂ is $C_{1-7}$-alkyl, aryl or aralkyl, preferably n-butyl, each of which is unsubstituted or substituted by $C_{1-4}$-alkyl, halogen or trihalomethyl; P₂ and P₃ are the same or different protecting groups for the hydroxyl groups; and ══ is a single bond or a double bond.

The following examples are used to further illustrate the present invention, but are not intended to limit the scope of the present invention. Any modifications or alterations that can be easily accomplished by persons skilled in the art fall within the scope of the disclosure of the specification and the appended claims.

EXAMPLES

Example 1

3-(((1S,2R,3R,5S)-3-(tert-butyldimethylsilyloxy)-2-((S,E)-3-(tert-butyldimethyl-silyloxy)oct-1-enyl)-5-(hydroxymethyl)cyclopentyl)methyl)phenol

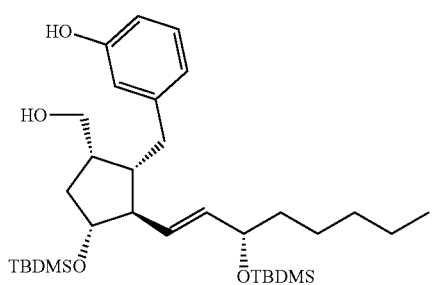 [SMILES: CCCCC[C@@H](/C=C/[C@@H]1[C@@H](Cc2cccc(O)c2)[C@@H](CO)C[C@H]1O[Si](C)(C)C(C)(C)C)O[Si](C)(C)C(C)(C)C]

A solution of (((1S,2S,3R,4R)-2-(3-(benzyloxy)benzyl)-4-(tert-butyldimethyl-silyloxy)-3-((S,E)-3-(tert-butyldimethylsilyloxy)oct-1-enyl)cyclopentyl)methanol (10 g, 15 mmol) in methanol (200 ml) was treated with potassium hydroxide (2.2 g, 40 mmol) and 5% Pd/C (1 g, 10% wt) under hydrogen for 1 hour. After the reaction was completed, the reaction mixture was filtered with celite pad and washed with methanol. Then, the pH value of the mixture was adjusted to 8.5 with 2M a sodium bisulfate aqueous solution. The solvent was evaporated. The resulting residue was dissolved in water and extracted with ethyl acetate. After separating, the organic layer was washed with brine and dried over anhydrous magnesium sulfate. The solid was filtered off. The organic solvent was evaporated off under vacuum. The crude product was purified by chromatography on silica gel using a mixture of hexane and ethyl acetate as a gradient eluent. Yield: 95%

$^1$H-NMR (CDCl$_3$): δ 7.107 (t, 1H), 6.732 (d, 1H), 6.697 (s, 1H), 6.650 (d, 1H), 6.348 (br s, 1H), 5.495-5.373 (m, 2H), 4.066-4.038 (m, 2H), 3.809 (s, 2H), 3.670-3.648 (m, 1H), 2.821-2.694 (m, 2H), 2.377-2.333 (m, 1H), 2.119-2.006 m, 3H), 1.605-1.246 (m, 9H), 0.907-0.856 (m, 21H), 0.079-0.031 (m, 12H)

$^{13}$C-NMR (CDCl$_3$): δ 56.150, 143.458, 135.018, 131.094, 129.424, 120.338, 115.776, 112.846, 79.183, 73.080, 63.547, 58.613, 49.239, 41.459, 40.533, 38.589, 34.642, 31.842, 25.929, 25.777, 25.101, 22.634, 18.300, 17.906, 14.042, −4.205, −4.463, −4.752, −4.805

Example 2

3-(((1S,2R,3R,5S)-3-((ter-butyldbutyldimethylsilyl)oxy)-2-((S,E)-3-((tert-butyldimethylsilyl) oxy)oct-1-en-1-yl)-5-(hydroxymethyl)cyclopentyl)methyl)phenyl methanesulfonate

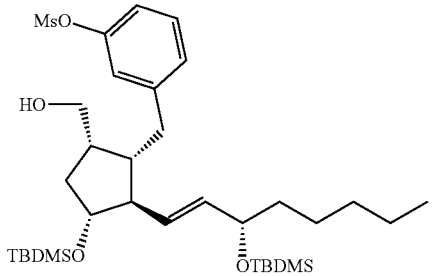 [SMILES: CCCCC[C@@H](/C=C/[C@@H]1[C@@H](Cc2cccc(OS(C)(=O)=O)c2)[C@@H](CO)C[C@H]1O[Si](C)(C)C(C)(C)C)O[Si](C)(C)C(C)(C)C]

A solution of 3-(((1S,2R,3R,5S)-3-(tert-butyldimethylsilyloxy)-2-((S,E)-3-(tert-butyldimethylsilyloxy)oct-1-enyl)-5-(hydroxymethyl)cyclopentyl)methyl)phenol (1.0 g, 1.7 mmol) in dichloromethane (30 ml) was treated with triethylamine (0.35 g, 3.5 mmol) and the reaction mixture was cooled to −10° C. Then, mesyl chloride (0.24 g, 2.0 mmol) was added into the mixture and the mixture was warmed to room temperature. After 30 minutes, the resulting mixture was cooled down to 0° C. and saturated sodium bicarbonate was poured into. The mixture solution was separated and the organic layer was washed with brine. The solvent was dried over anhydrous magnesium sulfate. The solid was filtered off. The organic solvent was evaporated off under vacuum. The crude product was purified by chromatography on silica gel. Yield: 90%.

$^1$H-NMR (CDCl$_3$): δ 7.294 (t, 1H), 7.169 (d, 1H), 7.127 (s, 1H), 7.090 (d, 1H), 5.463-5.353 (m, 2H), 4.062-4.020 (m, 2H), 3.719 (br s, 1H), 3.648-3.619 (m, 1H), 3.375 (br s, 1H), 3.112 (s, 3H), 2.851 (d, 2H), 2.377-2.342 (m, 1H), 2.117-1.973 (m, 3H), 1.608-1.256 (m, 9H), 0.896-0.850 (m, 21H), 0.073-0.031 (m, 12H)

$^{13}$C-NMR (CDCl3): δ 149.326, 144.536, 135.223, 130.927, 129.712, 127.693, 122.069, 119.177, 79.092, 72.928, 63.600, 58.484, 49.163, 41.565, 40.502, 38.597, 37.322, 34.491, 31.826, 29.261, 27.394, 25.906, 25.769, 25.063, 22.634, 18.278, 17.883, 14.035, 13.716, 8.736, −4.236, −4.463, −4.744, −4.812

Example 3

(1R,2R,3aS,9aS)-2-(tert-butyldimethylsilyloxy)-1-((S,E)-3-(tert-butyldimethyl-silyloxy) oct-1-enyl)-2,3,3a,4,9,9a-hexahydro-1H-cyclopenta[b]naphthalen-5-ol

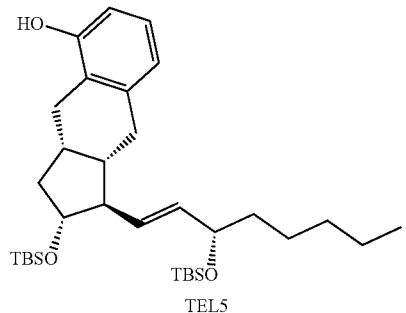 [SMILES: CCCCC[C@@H](/C=C/[C@@H]1[C@H]2Cc3cccc(O)c3C[C@H]2C[C@H]1O[Si](C)(C)C(C)(C)C)O[Si](C)(C)C(C)(C)C]

A solution of 3-(((1S,2R,3R,5S)-3-((tert-butyldimethylsilyl)oxy)-2-((S,E)-3-((tert-butyl dimethylsilyl)oxy)oct-1-en-1-yl)-5-(hydroxymethyl)cyclopentyl)methyl)phenyl methanesulfonate (0.5 g, 0.8 mmol) in anhydrous THF (7.5 ml) at −10° C. under nitrogen was treated with 60% sodium hydride (90 mg, 2.4 mmol). The resulting suspension was stirred over 16 hours at 70° C. The reaction was diluted with ice cold brine and extracted. The reaction mixture was phase separated and the aqueous layer was extracted with ethyl acetate. The organic layers were combined and dried over anhydrous magnesium sulfate. The solid was filtered off. The solvent was evaporated off under vacuum. The crude product was purified by chromatography on silica gel using a mixture of hexane and ethyl acetate as a gradient eluent. Yield: 87%.

$^1$H-NMR (CDCl3): δ 6.991 (t, 1H), 6.712 (d, 1H), 6.652 (d, 1H), 5.536-5.439 (m, 2H) 5.006 (br s, 1H), 4.150-4.081 (m, 1H), 3.809-3.746 (m, 1H), 2.672 (dt, 2H), 2.502 (dd, 1H), 2.429 (dd, 1H), 2.332-2.265 (m, 1H), 2.159-2.095 (m, 1H), 2.001-1.845 (m, 2H), 1.531-1.158 (m, 9H), 0.919-0.835 (m, 21H), 0.061-0.024 (m, 12H)

$^{13}$C-NMR (CDCl3): δ 52.514, 140.938, 135.094, 130.646, 126.213, 124.513, 120.619, 112.945, 73.149, 55.835, 41.406, 39.857, 38.658, 32.601, 32.221, 31.864, 25.959, 25.936, 25.192, 22.657, 18.278, 18.202, 14.073, −4.167, −4.494, −4.524, −4.706

We claim:
1. A process for preparing a compound of Formula 1:

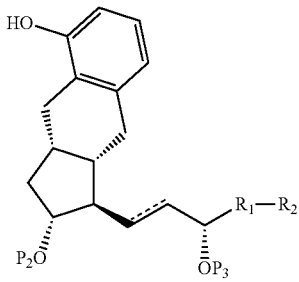

wherein $R_1$ is a single bond, $C_{1-4}$-alkylene or —$CH_2O$—; $R_2$ is $C_{1-7}$-alkyl, aryl or aralkyl, each of which is unsubstituted or substituted by $C_{1-4}$-alkyl, halogen or trihalomethyl; $P_2$ and $P_3$ are the same or different protecting groups for the hydroxyl groups; and ══ is a single bond or a double bond,
comprising reacting a compound of Formula 2:

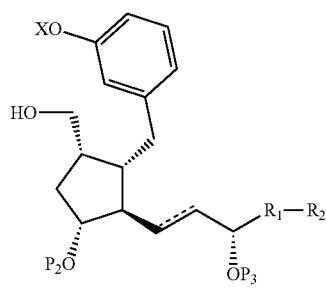

wherein X is a sulfonyl group; $R_1$, $R_2$, ══, $P_2$ and $P_3$ are as defined above, with a base.

2. The process according to claim 1, wherein the sulfonyl group is methanesulfonyl or p-toluenesulfonyl.

3. The process according to claim 1, wherein the base is selected from sodium hydride, potassium hydride, lithium hydride, potassium tert-butoxide and butyllithium.

4. A process for preparing a compound of Formula 1:

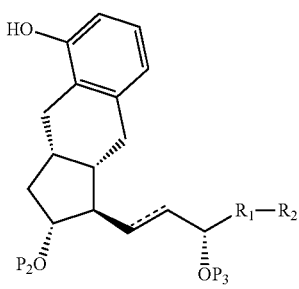

wherein $R_1$ is a single bond, $C_{1-4}$-alkylene or —$CH_2O$—; $R_2$ is $C_{1-7}$-alkyl, aryl or aralkyl, each of which is unsubstituted or substituted by $C_{1-4}$-alkyl, halogen or trihalomethyl; $P_2$ and $P_3$ are the same or different protecting groups for the hydroxyl groups; and ══ is a single bond or a double bond,
comprising the steps of
(a) sulfonylation of a compound of Formula 3

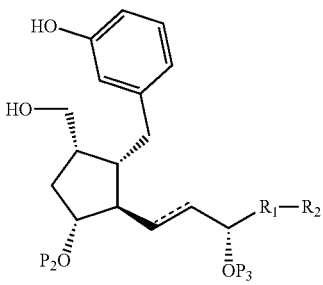

in the presence of a first base with a sulfonyl donor to form a compound of Formula 2,

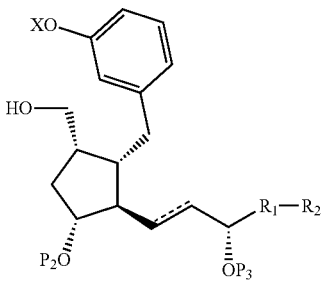

wherein X is a sulfonyl group; $R_1$, $R_2$, ══, $P_2$ and $P_3$ are as defined above, and
(b) intramolecular alkylation of the compounds of Formula 2 in the presence of a second base to form the compound of Formula 1.

5. The process according to claim 4, wherein the sulfonyl donor is methanesulfonyl chloride or p-toluenesulfonyl chloride.

6. The process according to claim 4, wherein the sulfonyl group is methanesulfonyl or p-toluenesulfonyl.

7. The process according to claim 4, wherein the first base is selected from sodium hydride, potassium hydride, lithium hydride, pyridine, triethylamine, N,N-Diisopropylethylamine and imidazole.

8. The process according to claim 4, wherein the second base is selected from sodium hydride, potassium hydride, lithium hydride, potassium tert-butoxide and butyllithium.

9. A compound of Formula 3

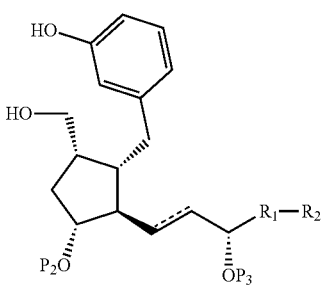

wherein $R_1$ is a single bond, $C_{1-4}$-alkylene or —$CH_2O$—; $R_2$ is $C_{1-7}$-alkyl, aryl or aralkyl, each of which is unsubstituted or substituted by $C_{1-4}$-alkyl, halogen or trihalomethyl; $P_2$ and $P_3$ are the same or different protecting groups for the hydroxyl groups, and ═ is a single bond or a double bond.

10. The compound of claim 9, wherein $R_1$ is methylene and $R_2$ is n-butyl.

\* \* \* \* \*